US006245366B1

(12) United States Patent
Popplewell et al.

(10) Patent No.: US 6,245,366 B1
(45) Date of Patent: Jun. 12, 2001

(54) FAT-COATED ENCAPSULATION COMPOSITIONS AND METHOD FOR PREPARING THE SAME

(75) Inventors: Lewis M. Popplewell, Cockeysville; Michael A. Porzio, Monkton, both of MD (US)

(73) Assignee: McCormick & Company, Inc., Sparks, MD (US)

( * ) Notice: Subject to any disclaimer, the term of this patent is extended or adjusted under 35 U.S.C. 154(b) by 0 days.

(21) Appl. No.: 09/284,948

(22) PCT Filed: Oct. 24, 1997

(86) PCT No.: PCT/US97/18709

§ 371 Date: Aug. 23, 1999

§ 102(e) Date: Aug. 23, 1999

(87) PCT Pub. No.: WO98/18338

PCT Pub. Date: May 7, 1998

Related U.S. Application Data

(60) Provisional application No. 60/029,621, filed on Oct. 25, 1996.

(51) Int. Cl.$^7$ ................................................... A23L 1/237

(52) U.S. Cl. .................. 426/96; 426/516; 426/649; 426/650; 426/658; 426/661; 426/806

(58) Field of Search ......................... 426/96, 516, 649, 426/650, 658, 661, 806, 804

(56) References Cited

U.S. PATENT DOCUMENTS

| | | |
|---|---|---|
| 1,696,419 | 12/1928 | Staudinger et al. . |
| 2,156,212 | 4/1939 | Wendt et al. . |
| 2,306,061 | 12/1942 | Johnston . |
| 2,809,895 | 10/1957 | Swisher . |

(List continued on next page.)

FOREIGN PATENT DOCUMENTS

| | | |
|---|---|---|
| 0 010 804 | 5/1980 | (EP) . |
| 0 028 043 | 5/1981 | (EP) . |
| 0 041 370 | 12/1981 | (EP) . |
| 0 144 758 | 6/1985 | (EP) . |
| 0 158 460 | 10/1985 | (EP) . |
| 0 201 968 | 11/1986 | (EP) . |
| 0 213 247 | 3/1987 | (EP) . |
| 0 353 806 | 2/1990 | (EP) . |
| 0 354 810 | 2/1990 | (EP) . |
| 1 249 250 | 10/1971 | (GB) . |
| 1538958 | 1/1979 | (GB) . |
| 2 063 640 | 6/1981 | (GB) . |
| 43 506 | 1/1974 | (IL) . |
| WO 93/19622 | 10/1993 | (WO) . |
| WO 94/06308 | 3/1994 | (WO) . |
| WO 94/23593 | 10/1994 | (WO) . |
| WO 96/07333 | 3/1996 | (WO) . |

OTHER PUBLICATIONS

Levine et al., "Glass transitions in Foods", pp. 82–21 in *Physical Chemistry of Foods*, H. Schwartzberg and R. Hartel, Eds., Marciel Decker, New York 1992.
Levine et al., "Water as a Plasticizer: physico–chemical aspects of low–moisture polymeric systems", pp. 79–185 in *Water Science Reviews*, vol. 3, Franks eds., Cambridge University Press, London 1988.
H. Heath, *Source Book of Flavors*, Avi Publishing Co., Westport, CT, 1981, pp. 148–287.
Roos et al., *J. Food Science*, vol. 56, No. 6, pp. 1676–1681, (1991).
S. L. Young et al., *J. Diary Science*, vol. 76, pp. 2868–2877 (1993).
Kirk–Othmer, *Encyclopedia of Chemical Technology*, 4$^{th}$ Ed., Wiley, New York, vol. 3, pp. 876–892 (1992).
Kirk–Othmer, *Encyclopedia of Chemical Technology*, 3$^{rd}$ Ed., Wiley, New York, vol. 15, pp. 522–570 (1981).
J. A. Maga, et al., *Dev. Food Sci.*, vol. 29, pp. 519–525 (1992).
A.P. Hansen et al., *J. Dairy Sci.*, vol. 74, pp. 2936–2940 (1991).
S. L. Young et al, *J. Dairy Sci.*, vol. 76, pp. 2878–2885 (1993).
P. K. W. Ng et al, *Journal of Food Sci.*, vol. 54, pp. 105–107 (1989).
T. E. O'Neill et al, *Agric. Food Chem.*, vol. 35, pp. 770–774 (1987).
A.P. Hansen et al, *ACS Symposium Series: Barrier Polymer Structure*, ACS, Washington, DC, Chapter 17, pp. 318–332 (1990).
T. E. O'Neill et al, *Journal of Food Sci.*, vol. 52, pp. 98–101 (1987).
D. L. Moreau et al, *Food Structure*, vol. 12, pp. 457–468, (1993) (Abstact only).
T. E. O'Neill et al, *J. Food Sci.*, vol. 53, pp. 906–909 (1988) (Abstract only).
S. R. Noar, *Dissertation Abstracts Int.*, B, vol. 46(9) 2893 (1986) order No. DA8525804 (Abstract only).
J.P. Dumont et al, *J. Agric. Food Chem.*, vol. 34, pp. 1041–1045 (1986) (Abstract only).
E. Jasinksi et al, *Milchwissenschaft*, vol. 40, pp. 596–599 (1985) (Abstract only).
O.E. Mills et al, *Lebensm. –Wiss.*, vol. 17, pp. 331–335 (1984) (Abstract only)).
S. Arai et al, *Agricultural and Biological Chemistry*, vol. 34, pp. 1569–1573 (1970) (Abstract only).
Kirk–Othmer, *Encyclopedia of Chemical Technology*, 3rd Ed., Wiley, New York, vol. 11, pp. 490–498 (1980).
Kirk–Othmer *Encyclopedia of Chemical Technology*, 3rd Ed., Wiley, New York, vol. 11, pp. 146–163 (1980).

*Primary Examiner*—Carolyn Paden
(74) *Attorney, Agent, or Firm*—Oblon, Spivak, McClelland, Maier & Neustadt, P.C.

(57) ABSTRACT

Fat-coated encapsulation compositions may be prepared by: (i) mixing an active agent with a molten fat, to obtain a slurry, and (ii) cooling the slurry, to obtain a solid mass in which the active agent is dispersed in solid fat.

37 Claims, No Drawings

U.S. PATENT DOCUMENTS

| | | |
|---|---|---|
| 2,856,291 | 10/1958 | Schultz . |
| 2,857,281 | 10/1958 | Schultz et al. . |
| 2,919,989 | 1/1960 | Schultz . |
| 3,021,218 | 2/1962 | Clinton et al. . |
| 3,041,180 | 6/1962 | Swisher . |
| 3,315,803 | 4/1967 | Dame et al. . |
| 3,410,180 | 11/1968 | Spangler et al. . |
| 3,532,515 | 10/1970 | Broderick et al. . |
| 3,625,709 | 12/1971 | Mitchell . |
| 3,655,397 | 4/1972 | Parliment et al. . |
| 3,704,137 | 11/1972 | Beck . |
| 3,783,163 | 1/1974 | Patel . |
| 3,796,814 | 3/1974 | Cermak . |
| 3,821,447 | 6/1974 | Jasovsky et al. . |
| 3,823,241 | 7/1974 | Patel et al. . |
| 3,852,481 | 12/1974 | Feldman et al. . |
| 3,857,964 | 12/1974 | Yolles . |
| 3,873,746 | 3/1975 | Mahlmann . |
| 3,922,354 | 11/1975 | Galuzzi et al. . |
| 3,922,375 | 11/1975 | Dalan et al. . |
| 3,939,291 | 2/1976 | Katz . |
| 3,949,094 * | 4/1976 | Johnson ............................ 426/471 |
| 3,970,765 | 7/1976 | Pitchon et al. . |
| 3,970,766 | 7/1976 | Mitchell et al. . |
| 3,971,852 | 7/1976 | Brenner et al. . |
| 3,973,046 | 8/1976 | Mol . |
| 3,979,528 | 9/1976 | Mahlmann . |
| 3,985,910 | 10/1976 | Kirkpatrick . |
| 3,989,852 | 11/1976 | Palmer . |
| 3,991,223 | 11/1976 | Baron et al. . |
| 4,004,039 | 1/1977 | Shoaf et al. . |
| 4,007,291 | 2/1977 | Siedlecki et al. . |
| 4,008,340 | 2/1977 | Kung et al. . |
| 4,044,167 | 8/1977 | Jolly et al. . |
| 4,086,367 | 4/1978 | Ziccarelli . |
| 4,119,736 | 10/1978 | Howland et al. . |
| 4,218,262 * | 8/1980 | Warren ............................... 106/206 |
| 4,230,687 | 10/1980 | Sair et al. . |
| 4,232,047 | 11/1980 | Sair et al. . |
| 4,289,794 | 9/1981 | Kleiner et al. . |
| 4,335,149 | 6/1982 | Stipp . |
| 4,343,826 | 8/1982 | McNaught . |
| 4,378,380 | 3/1983 | Scarpellino et al. . |
| 4,388,328 | 6/1983 | Glass . |
| 4,398,422 | 8/1983 | Haerten . |
| 4,473,620 * | 9/1984 | Wu ................................. 428/402.24 |
| 4,508,745 | 4/1985 | Fulger et al. . |
| 4,520,033 | 5/1985 | Tuot . |
| 4,532,145 | 7/1985 | Saleb et al. . |
| 4,547,377 | 10/1985 | Ogawa et al. . |
| 4,551,345 | 11/1985 | Davidescu et al. . |
| 4,556,575 | 12/1985 | Katz et al. . |
| 4,574,089 | 3/1986 | Musto et al. . |
| 4,608,340 | 8/1986 | Szajani et al. . |
| 4,610,890 | 9/1986 | Miller et al. . |
| 4,659,390 | 4/1987 | Zeller et al. . |
| 4,678,516 | 7/1987 | Alderman et al. . |
| 4,689,235 | 8/1987 | Barnes et al. . |
| 4,690,825 | 9/1987 | Won . |
| 4,698,264 | 10/1987 | Steinke . |
| 4,707,367 | 11/1987 | Miller et al. . |
| 4,738,724 | 4/1988 | Wittwer et al. . |
| 4,820,534 | 4/1989 | Saleeb et al. . |
| 4,820,634 | 4/1989 | Watanabe . |
| 4,879,130 | 11/1989 | Heyland et al. . |
| 4,919,962 | 4/1990 | Arora et al. . |
| 4,999,208 | 3/1991 | Lengerich et al. . |
| 5,009,900 | 4/1991 | Levine et al. . |
| 5,035,908 | 7/1991 | Arora et al. . |
| 5,043,169 * | 8/1991 | Cherukuri ............................ 426/453 |
| 5,064,669 * | 11/1991 | Tan ....................... 426/650 |
| 5,079,026 | 1/1992 | Arora et al. . |
| 5,087,461 | 2/1992 | Levine et al. . |
| 5,098,893 | 3/1992 | Franks et al. . |
| 5,124,162 | 6/1992 | Boskovic et al. . |
| 5,194,262 * | 3/1993 | Goldberg ............................ 424/401 |
| 5,266,335 | 11/1993 | Cherukuri et al. . |
| 5,271,934 * | 12/1993 | Goldberg ............................ 424/401 |
| 5,354,559 | 10/1994 | Morehouse . |
| 5,370,881 | 12/1994 | Fuisz . |
| 5,399,368 | 3/1995 | Garwood et al. . |
| 5,401,518 | 3/1995 | Adams et al. . |
| 5,460,756 * | 10/1995 | Redding ............................... 264/4 |
| 5,525,367 * | 6/1996 | King ...................... 426/533 |
| 5,536,513 | 7/1996 | Graf et al. . |
| 5,601,760 | 2/1997 | Rosenberg . |
| 5,601,865 | 2/1997 | Fulger et al. . |
| 5,603,971 | 2/1997 | Porzio et al. . |
| 5,750,178 | 5/1998 | Cheng et al. . |
| 5,756,136 | 5/1998 | Black et al. . |
| 5,792,505 | 8/1998 | Fulger et al. . |
| 5,866,189 * | 2/1999 | Garwood ............................ 426/573 |
| 5,897,897 | 4/1999 | Porzio et al. . |
| 5,922,388 * | 7/1999 | Garwood ............................ 426/574 |
| 5,958,502 | 9/1999 | Fulger et al. . |
| 6,051,540 * | 4/2000 | Shefer ............................... 510/101 |
| 6,090,419 | 7/2000 | Popplewell et al. . |
| B1 5,460,756 * | 5/2000 | Redding ............................... 264/4 |

* cited by examiner

FAT-COATED ENCAPSULATION COMPOSITIONS AND METHOD FOR PREPARING THE SAME

This application is the National Stage of International Application No. PCT/US97/18709, filed Oct. 24, 1997 and claims the benefit of U.S. Provisional Application No. 60/029,621, filed Oct. 25, 1996.

BACKGROUND OF THE INVENTION

1. Field of the Invention

The present invention relates to fat-coated encapsulation compositions in which an active agent or other solid is encapsulated in fat. The present invention also relates to a method for preparing such compositions.

2. Discussion of the Background

The encapsulation of active agents, such as flavorants, is in general well known. Conventional techniques for the encapsulation of active agents include spray drying, melt extrusion, coacervation, and freeze drying.

Encapsulation employing the spray drying process requires that the active agent or encapsulant, in the form of an aqueous emulsion/solution with solubilized carrier solids, be fed into the spray dryer, atomized and dispersed into a heated air chamber plenum, dried, and collected. The resulting product is obtained as a fine particulate with the active agent dispersed within the porous particle matrix either as discrete droplets/particles or essentially dissolved in the matrix. The carrier solutes used in the emulsion preparation are required not only to have emulsifying properties but also be bland, exhibit a high degree of solubility with low intrinsic viscosity, be non-reactive with the flavor load while retaining volatile components, and exhibit stable powder properties once dried. In almost all commercial production formulas the carrier solutes of choice are usually selected for their emulsifying function and high degree of solubility.

It is well known by those skilled in spray drying processes that retention of volatiles is improved with increased dissolved solids levels in the aqueous phase of the emulsion. This requirement generally restricts spray drying encapsulation formulations to the use of highly water-soluble, modified starches, such as the octenylsuccinate-derivatized modified starches, or gum arabic as the emulsifying, film-forming carrier polymer component. Soluble, inert carrier components such as sugars, corn syrup solids and maltodextrins are added to the aqueous flavor emulsion in order to increase the solid level, lower ingredient cost, increase yield, and improve product stability.

The spray drying encapsulation process is relatively simple, economical, and easily scaled to large production volumes. A major benefit of spray drying encapsulation is the broad range of flavors and flavoring systems which can be prepared. These flavorings include oil-soluble flavors, water-soluble compounds, natural extracts, single component flavor compounds, as well as complex compounded flavors having both water- and oil-soluble components.

Yet another technique which has been employed is that of melt extrusion of materials in carbohydrate matrices. In this application, a carbohydrate melt is prepared and the encapsulate is added. The resulting solution is introduced into a quenching medium to produce a solid carbohydrate product containing the flavor. This technique while successful, is again, limited to comparatively high boiling point flavors because the carbohydrate solution is produced and delivered to the quenching medium at elevated temperatures. This technique inherently can result in the loss of some of the low boiling point constituents in the flavor. Because of such losses, it is common to enhance the flavorant by adding extra low-boiling components.

Coacervation encapsulation, a technology commercialized in the 1950s, yields true controlled release functionality and has found wide usage in the pharmaceutical, fragrance and specialty products industries. However the relatively high process costs, sensitive multi-step batch process, regulations limiting the number of polymeric agents which can be used in food preparations, and the difficulty in dealing with encapsulates having both aqueous and lipid solubility properties has drastically limited the application of coacervation for flavor encapsulation in the food industry. A general discussion of these issues is provided by R. Versic, "Coacervation for Flavor Encapsulation," in *Flavor Encapsulation, American Chemical Society Symposium Series* #370, S. Risch and G. Reneccius, Eds., Chapter 14, 1988, which is incorporated herein by reference.

Coacervation microcapsule systems can be generated in the form of simple coacervates, which are derived from a single polymer species in solution. Complex coacervates, which require the interaction of two distinct and oppositely charged polymer species, are also well characterized.

Freeze-drying solutions of matrix materials containing either dissolved or dispersed flavors has also been used to produce encapsulated flavors. These methods generally result in losses of highly volatile components, and products having a foamy, porous structure.

Spray-chilling is another form of encapsulation practiced commercially. This process begins with mixing a liquid flavor into a molten fat to create a solution/dispersion. The resulting mixture is then atomized into a chamber where it is contacted with an air stream which is cool enough to cause the atomized droplets to solidify, thus forming a crude encapsulated product. The major drawbacks of spray-chilling include fat/active-agent interactions, volatilization over time of lipid soluble materials, as well as loss of volatile materials during processing.

Although all of the conventional encapsulation techniques afford a certain degree of protection to the active agent, in many circumstances it is desired to increase the degree of protection. For example, certain active agents, e.g., vitamins and essential oils, which are sensitive to degradation on exposure to water or the atmosphere may degrade over time even when encapsulated by one of the above-mentioned techniques. Additionally, when encapsulated products are used in final applications, they often must withstand significant environmental challenges.

When it is desired to improve the degree of protection afforded by the above-mentioned encapsulation techniques, the technique of coating the encapsulation composition with a fat coating has been employed. Conventionally, such fat coatings are applied via a fluidized bed technique. This technique suffers from serious shortcomings. For example, exposure of the active agent to a vigorous air stream is one concern when using the fluidized bed technique, as many commercially significant active agents may either volatilize or oxidize under such conditions. This air contacting may occur over a long time period as the rate of fat addition must often be slow, as it is determined by the heat load the air stream can carry away. This also limits the overall productivity of fluid-bed techniques, which in turn influences processing costs and ultimately commercial utility. In addition, the protection afforded by fat coatings applied as described above, or using any method, may be easily lost when the fat-coated particle is exposed to temperatures above the melting point of the fat.

Thus, there remains a need for a method of applying a fat coating to an active agent or other solid which does not suffer from the above-described drawbacks. There also remains a need for fat-coated encapsulation compositions which afford increased protection for the active agent, or solid and for a method of producing such fat-coated encapsulation compositions.

SUMMARY OF THE INVENTION

Accordingly, it is one object of the present invention to provide novel fat-coated encapsulation compositions.

It is another object of the present invention to provide novel fat-coated encapsulation compositions which afford increased protection of the encapsulant.

It is another object of the present invention to provide a method for producing such fat-coated encapsulation compositions.

These and other objects, which will become apparent during the following detailed description, have been achieved by the inventor's discovery that a fat coating may be applied to an active agent or other solid by:

(i) mixing an active agent, with a molten fat, to obtain a slurry; and (ii) cooling the slurry, to obtain a solid in which the active agent is dispersed in solid fat.

The inventor has also discovered that a stable slurry of the active agent or other solid in the molten fat may be obtained even when the active agent has a fairly high density, such as encapsulated active agents produced by melt extrusion, by including agents to increase the apparent viscosity and/or density of the slurry during or prior to the mixing step.

The inventor has further discovered that the density of the final fat-coated product may be adjusted by adding a density-modifying agent.

The inventor has further discovered that the addition of an agent which causes the molten fat to gel affords a fat-coated encapsulation composition which provides increased protection to the active agent.

DETAILED DESCRIPTION OF THE PREFERRED EMBODIMENTS

Thus, in a first embodiment the present invention provides novel fat-coated encapsulation compositions. In the present fat-coated encapsulation compositions, an active agent is coated with a layer of fat.

The term active agent, as used in the present invention, includes agents such as medications, pesticides, preservatives, vitamins, flavoring agents, perfumery chemicals and fragrances, and food colorants both synthetic and natural. Suitable medications include antacids, anti-inflammatory substances, coronary vasodilators, cerebral vasodilators, peripheral vasodilators, anti-infectives, psychotopics, antimanics, stimulants, antihistamines, laxatives, decongestants, vitamins, gastrointestinal sedatives, antidiarrheal preparations, antianginal drugs, antiarrhythmics, antihypertensive drugs, vasoconstrictors, migraine treatments, anticoagulants, antithrombotic drugs, analgesics, antipyretics, hypnotics, sedatives, antiemetics, antinauseants, anticonvulsants, neuromuscular drugs, hyper- and hypo-glycaemic agents, thyroid and antithyroid preparations, diuretics, antispasmodics, uterine relaxants, mineral and nutritional additives, antiobesity drugs, anabolic drugs, erythropoietic drugs, antiasthmatics, expectorants, cough suppressants, mucolytics, antiuricemic drugs and other drug substances such as topical analgesics, local anesthetics, and the like.

Suitable pesticides include insecticides, nematocides, fungicides, herbicides and microbicides. Insecticides which may be encapsulated in the present compositions include those disclosed in Kirk-Othmer, *Encyclopedia of Chemical Technology*, 4th Ed., vol. 14, Wiley, N.Y., pp. 524–602 (1995), which is incorporated herein by reference. Suitable nematocides include, e.g., methyl N',N'-dimethyl-N-((methylcarbamoyl)oxy]-1-thiooxamimidate (oxamyl) and those disclosed in Kirk-Othmer, *Encyclopedia of Chemical Technology*, 3rd Ed., vol. 18, Wiley, N.Y., pp. 305–8 (1982), which is incorporated herein by reference. Suitable fungicides include those disclosed in Kirk-Othmer, *Encyclopedia of Chemical Technology*, 4th Ed. vol. 12, Wiley, N.Y., pp. 204–227 (1994), which is incorporated herein by reference. Suitable herbicides include those disclosed in Kirk-Othmer, *Encyclopedia of Chemical Technology*, 4th Ed., vol. 13, Wiley, N.Y., pp. 73–136 (1995), which is incorporated herein by reference. Suitable antibiotics and antimicrobials include those disclosed in Kirk-Othmer, *Encyclopedia of Chemical Technology*, 4th Ed., vol. 2, Wiley, N.Y., pp. 854–1018 (1992) and vol. 3, pp. 1–346 (1992), both of which are incorporated herein by reference. Suitable vitamins include those disclosed in Kirk-Othmer, *Encyclopedia of Chemical Technoloqy*, 3rd Ed. vol. 24, Wiley, N.Y., pp. 1–277 (1984), which is incorporated herein by reference. Suitable food additives, in addition to flavoring agents, include those disclosed in Kirk-Othmer, *Encyclopedia of Chemical Technology*, 4th Ed., vol. 11, Wiley, N.Y., pp. 805–833 (1994), which is incorporated herein by reference.

Suitable colorants are described in Marmion, D. M., *Handbook of U.S. Colorants for Foods, Drugs, and Cosmetics*, John Wiley & Sons, Inc., New York and include precipitated soluble dyes on insoluble substratum (Lakes). Lake substrata include: alumina, blanc fixe, gloss white, clay, titanium dioxide, zinc oxide, talc, rosin, aluminum benzoate, calcium carbonate, or any combination of two or more of these materials. Dyes include FD&C dyes Blue 1, Blue 2, Green 3, Red 3, Red 4, Red 40, Yellow 5, Yellow 6, Citrus Red 2, orange B; D&C dyes Blue 4, Blue 6, Blue 9, Brown 1, Green 5, Green 6, Green 8, orange 4, Orange 5, Orange 10, Orange 11, Orange 17, Red 6, Red 7, Red 8, Red 9, Red 17, Red 19, Red 21, Red 22, Red 27, Red 28, Red 30, Red 31, Red 33, Red 34, Red 36, Red 37, Red 39, Violet 2, Yellow 7, Yellow 8, Yellow 10, Yellow 11, Ext Violet 2, Ext. Yellow 7, and [Phthalocyaninato (2-)] copper. Other colorants include: alumina, aluminum powder, annatto, beet powder, bismuth oxchloride, bronze powder, canthaxanthin, caramel, carmine, chromium-cobalt-aluminum oxide, chromium hydroxide, chromium hydroxide green, copper powder, dihydroxyacetone, ferric ammonium citrate, ferric ammonium ferrocyanide, guanine, dried algae meal, ferrous gluconate, fruit juice, grape skin extract, logwood extract, mica, paprika, potassium sodium copper chlorophyllin, pyrogallol, prophyllite, saffron, iron oxide, tagetes meal, talc, titanium dioxide, turmeric, ultramarine blue, vegetable juice, and zinc oxide.

The term flavoring agent includes spice oleoresins derived from allspice, basil, capsicum, cinnamon, cloves, cumin, dill, garlic, marjoram, nutmeg, paprika, black pepper, rosemary and tumeric; essential oils: anise oil, caraway oil, clove oil, eucalyptus oil, fennel oil, garlic oil, ginger oil, peppermint oil, onion oil, pepper oil, rosemary oil, spearmint oil; citrus oils: orange oil, lemon oil, bitter orange oil and tangerine oil; alliaceous flavors: garlic, leek, chive, and onion; botanical extracts: arnica flower extract, chamomile flower extract, hops extract, and marigold extract; botanical flavor extracts: blackberry, chicory root, cocoa, coffee, kola, licorice root, rose hips., sarsaparilla root, sassafras bark, tamarind and vanilla extracts; protein hydrolysates: hydrolyzed vegetable protein (HVP's), meat protein hydrolyzates, milk protein hydrolyzates; and compounded flavors both natural and artificial including those disclosed in S. Heath, *Source Book of Flavors*, Avi Publishing Co., Westport, Conn., 1981, pp. 149–277.

In the method of the present invention, an active agent is coated with fat. The active agent may be in the form of a solid, liquid, or paste. Preferably, the active agent is in the form of a solid or paste, more preferably a solid. Thus, when the active agent is a solid it may be used as is in the present method. However, when the active agent is a liquid, it is preferably but not necessarily encapsulated. Even solid active agents can be encapsulated prior to mixing with the molten fat and this is preferred, although not necessary.

The active agent may be encapsulated by any conventional technique, including spray drying, melt extrusion, coacervation, and freeze drying. Spray drying is described in Masters, K., *Spray Drying Handbook*, Third Edition, Halsted Press, John Wiley & Sons, Inc., New York, 1979, and Filkova, I and Mujumdar, A. S., "Industrial Spray Drying Systems," *Handbook of Industrial Drying*, Second Edition, A Mujumdar, Ed., pp 263–308, 1995, all of which are incorporated herein by reference.

Melt extrusion is described in U.S. Pat. Nos. 4,610,890, 4,707,367, 5,009,900, 4,820,534, 4,232,047, and 4,689,235, all of which are incorporated herein by reference.

Coacervation is described in R. Versic, "Coacervation for Flavor Encapsulation,." in *Flavor Encapsulation, American Chemical Society Symposium Series*, #370, S. Risch and G. Reneccius, Eds., American Chemical Society, Washington, D.C., Chapter 14, 1988; C. Thies, "Physicochemical Aspects of Microencapsulation," Polymer-Plastic Technology and Engineering, Vol. 5(1), pp. 1–22 (1975); C. Thies, in *Encyclopedia of Polymer Science and Engineering*, 2nd Ed., Vol. 9, pp. 7424–7451 (1987); and *Theory and Practice of Industrial Pharmacy*, L. Lachman, H. Lea and J. Kanig, Eds., Lea and Feiberger, Philadelphia, Pa., pp. 412–429, 1988, all of which are incorporated herein by reference.

Freeze drying is described in Liapis, A. I. and Bruttini, R. "Freeze Drying," *Handbook of Industrial Drying*, Second Edition, A Mujumdar, Ed., pp. 309–344, which is incorporated herein by reference.

The chemical and physical properties of the encapsulated active agent will depend on the matrix and method used for encapsulation, as well as the identity of the active agent itself. For example, encapsulated active agents prepared by spray drying will typically have a particle size of 5 to 200 $\mu$m and a density of 1 to 1.4 g/cm$^3$.

In contrast, encapsulated active agents prepared by melt extrusion will typically have a density of 1 to 1.5 g/cm$^3$. In the case of melt extrusion, the particle size may be freely varied by selection of an appropriate comminution technique, but particle sizes of 100 to 1500 $\mu$m are typical.

For the purposes of the present method, the active agent is preferably a solid, particulate material having a mean particle diameter of 0.1 $\mu$m to 1500 $\mu$m.

The fat used in the present compositions and methods may be any fat with a melting point above ambient temperature (20° C.), preferably 30 to 90° C. Examples of suitable fats include coconut oil, palm kernel oil, lard, tallow, hydrogenated forms of liquid oils such as soybean oil, cottonseed oil, canola oil, corn oil, peanut oil, olive oil, butter oil, and chicken fat. Preferred fats include hydrogenated, high-melting point fractions of soybean, cottonseed, and corn oils.

The method for preparing the present fat-coated encapsulation compositions involves first melting the fat. Typically, the fat is heated to a temperature which is 10 to 50° C. above its melting point. Then the active agent is added to the molten fat, and the mixture is agitated to obtain a slurry.

Any suitable heating means may be used to melt the fat, and any suitable mixing means may be used to form the slurry. Examples of suitable mixing means include food processors, blenders, kettles, scraped surface heat exchangers, extruders, and mixing tanks. Alternatively, it is possible to mix solid fat with the active agent and then heat and agitate to form the slurry.

Typically, the fat and encapsulated active agent will be mixed in a fat: encapsulated active agent weight ratio of 1:3 to 999:1, preferably 1:2 to 3:1.

After the formation of the slurry is complete, the slurry is then cooled to obtain a solid mass in which the encapsulated active agent is dispersed in the solid fat. Although it is possible to store and use the solid mass as obtained, for many applications, including the blending of foods or seasonings, it is preferable to form the slurry into particles during cooling by either spray-chilling or preferably flaking. Whatever cooling/solidification technique is used, comminution of the solid mass to obtain particles of the desired size in which the encapsulated active agent or other solid is coated with a layer of fat may be carried out. Typically, the comminution will be carried out to obtain fat-coated encapsulation composition particles having a size of 100 to 1500 $\mu$m, preferably 200 to 1000 $\mu$m. Any suitable comminution device may be used, such as Comil (Quadro Co.), Fitzmill (Fitzpatrick Co.), Reitzmill, Comitrol (Urschel Co.), or any food mill.

Preferably, the comminution is carried out such that a majority of the particles comprise one or more encapsulated active agent particles-which is completely coated with fat, i.e. has no exposed surface.

Many active agents may have particle densities which are significantly greater than the molten fat. These particles may also have a size such that the viscosity of the molten fat is insufficient to maintain them in suspension for even short periods without mixing. This greatly complicates processing.

In order to provide for the suspension of particles of this type, agents may be added to the molten fat which serve to increase the density of the agent/fat mixture and/or increase the apparent viscosity of the agent/fat mixture. These agents are solids which are not soluble in the molten fat, and may include sugars (sucrose, dextrose), dextrins, starches, proteins, gums, hydrocolloids, salts, celluloses, minerals, and silicas. Depending on the actual solid density of the material and the method of formation, these solids may have particle densities of 0.25 g/cm$^3$ to 5 g/cm$^3$, and particle sizes of 0.1 $\mu$m to 500 $\mu$m. Typically, the agent may be used at a fat: agent weight ratio of from 9:1 to 1:1, although other ratios are possible. The solids may be added at any appropriate step in the slurry formation.

An additional benefit of using the densifying/viscosity increasing agents is related to the density and structure of the final product. Since the agents increase the density of the molten fat mixture, they have a similar effect on the final product. This increase in density may be very useful in producing a particle that fits a particular application. Additionally, the densifying/viscosity increasing agent may result in a particle of increased hardness. This may give both benefits in the final application, as well as in processing.

A further benefit is related to the fact that the densifying/viscosity increasing agent may be selected so as to have specific functional properties in the final application. For example, if a sugar is used as the densifying agent, when the active agent is released via melting of the fat, the sugar will also be released. The sugar may thus be available for flavor enhancement, reaction, etc. A second example is the use of a gelatin as the densifying agent. If gelatin is released from the fat in an aqueous environment along with the active agent, it will be available to form a gel, thus potentially providing additional protection to the active agent.

In another embodiment, it is possible to dissolve ethylcellulose into the fat either directly via heating and/or by means of a co-solvent. This has two independent benefits. First, it increases the viscosity of the molten fat substantially, thus making it easier to suspend particles of active agent. Second, once solidified, the fat encapsulated composition may be heated above the melting point of the fat and the fat will retain a gel-like consistency (i.e., will not flow); thus affording increased protection to the active agent, by maintaining it in the hydrophobic lipid environment.

Typically, the ethylcellulose is added to the fat and dissolved via heating and/or by use of a cosolvent prior to addition of the active agent. In cases where the active agent can tolerate the process of dissolving the ethylcellulose, it may be present. Typically the fat:ethylcellulose weight ratio will range from 1:1 to 99:1, although other ratios are possible.

Other features of the invention will become apparent in the course of the following descriptions of exemplary embodiments which are given for illustration for the invention and are not intended to be limiting thereof.

EXAMPLES

Example 1

A fat encapsulated flavor was made by heating 340.5 grams of partially hydrogenated vegetable oil (Kaorich—Van den Bergh Foods) and 340.0 grams of partially hygrogenated cottonseed oil (07 Stearine Flakes—Quest Intl.) to approximately 200° F. in a jacketed kettle. 681 grams of spray-dried chocolate flavor was then added and mixed to attain a temperature of approximately 180° F. This mixture was then poured onto a Flaker equipped with a single applicator roll (2'×3' model Blaw-Knox) for solidification. The resulting flake product was then size-reduced via blending, sieved through a US 12 mesh screen and collected. This resulted in a small flake, easy to incorporate into products.

Example 2

A fat encapsulated color was made by heating 51 grams of partially hydrogenated vegetable oil (Kaorich—Van den Bergh Foods), 51 grams of partially hygrogenated cottonseed oil (07 Stearine Flake—Quest Intl.), 94 grams of maltodextrin (M100-Grain Products Corp.), and 4 grams of FD&C Blue #2 Lake to melting in a pan over gentle heat with stirring. This uniform suspension was then poured onto foil and allowed to solidify. The resulting product was then milled and sieved to obtain −10/+25 mesh and −25 mesh fractions. Both were placed in ambient temperature water at a level of approximately 4%. No bleeding of color was observed visually upon standing 2 days.

Example 3

A fat encapsulated flavor may be made by heating 19 parts of partially hydrogenated vegetable oil (Kaorich—Van den Bergh Foods) and 1 part ethylcellulose (EthoCel 100—Dow Chemical) to approximately 380° F. in a pan or kettle. The resulting mixture will be essentially clear and viscous, indicating dissolution of the ethylcellulose. The mixture may be cooled if desired to approximately 280° F. before adding 6.67 parts of spray-dried flavor and mixing to attain a viscous, reasonably uniform suspension. This mixture may then be solidified using any suitable means. The resulting product may then be size-reduced and sieved to obtain the final product. When placed in 200° F. water, this material will retain its piece identity.

Example 4

A modified fat composition matrix is prepared as follows: 10 grams of Ethocel (Ethylcellulose, 20 cps viscosity grade, Dow Chemical Company) are dispersed in 90 grams of a liquid acetylated monoglyceride (Cetodan 90-40, Grindsted Products). The 10% ethylcellulose mixture is heated at 100° C. until a clear, viscous phase is obtained. 50 parts of the ethylcellulose solution is added to 50 parts of premelted high melting fat (Durkee, KLX flakes). The system is stirred to assist mixing and the ethylcellulose-acetylated monoglyceride-fat phase allowed to cool quiescently. A hard solid fat is obtained. When this material is contacted with 90° C. hot water, the material remains as a semisolid and does not flow.

Example 5

A modified fat composition is-prepared as follows: 50 parts of a hard fat (Durkee, KLX flakes) are placed in a beaker and melted on a hot plate. Then 10 parts of Ethocel (20 cps) are dispersed in 40 parts of a liquid acetylated monglyceride (Cetodan 90-40, Grindsted Products), and the mixture is heated to approximately 140° C. A clear liquid phase is obtained which when cooled forms a very hard solid. The material is resistant to hot water and does not melt to a liquid form when placed in boiling water.

Obviously, numerous modifications and variations of the present invention are possibloe in light of the above teachings. It is therefore to be understood that, within the scope of the appended claims, the invention may be practiced otherwise than as specifically described herein.

What is claimed is:

1. A method for preparing a fat-coated encapsulation composition, comprising:
   (i) mixing an active agent with a molten fat, to obtain a slurry;
   (ii) cooling said slurry, to obtain a solid mass in which said active agent is dispersed in solid fat; and
   (iii) comminuting said solid mass,
wherein a densifying agent is present during said mixing and cooling.

2. The method of claim 1, wherein said solid mass is comminuted to a particle size of 10 $\mu$m to 2000 $\mu$m.

3. The method of claim 1, wherein said fat is selected from the group consisting of coconut oil, palm kernel oil, lard, tallow, hydrogenated forms of liquid oils such as soybean oil, cottonseed oil, canola oil, corn oil, peanut oil, olive oil, butter oil, and chicken fat.

4. The method of claim 1, wherein said active agent is an encapsulated active agent prepared by encapsulating said active agent by a method selected from the group consisting of spray drying, melt extrusion, coacervation, freeze drying, drum drying, belt drying, tray drying, tunnel drying, and extrusion.

5. The method of claim 1, wherein said densifying agent is selected from the group consisting of sugars, dextrins, starches, proteins, gums, hydrocolloids, salts, celluloses, minerals, and silicas.

6. The method of claim 1, wherein ethylcellulose is present during said mixing and said cooling.

7. A fat-coated flavor encapsulation composition, prepared by a method comprising:
   (i) mixing an active agent with a molten fat, to obtain a slurry;
   (ii) cooling said slurry, to obtain a solid mass in which said active agent is dispersed in solid fat; and
   (iii) comminuting said solid mass,
wherein said solid mass is comminuted to a particle size of 10 $\mu$m to 2000 $\mu$m.

8. The composition of claim 7, wherein said fat is selected from the group consisting of coconut oil, palm kernel oil, lard, tallow, hydrogenated forms of liquid oils such as soybean oil, cottonseed oil, canola oil, corn oil, peanut oil, olive oil, butter oil, and chicken fat.

9. The composition of claim 7, wherein said active agent is an encapsulated active agent prepared by encapsulating said active agent by a method selected from the group consisting of spray drying, melt extrusion, coacervation, freeze drying, drum drying, belt drying, tray drying, tunnel drying, and extrusion.

10. The composition of claim 7, wherein a densifying agent is present during said mixing and said cooling.

11. The composition of claim 10, wherein said densifying agent is selected from the group consisting of sugars, dextrins, starches, proteins, gums, hydrocolloids, salts, celluloses, minerals, and silicas.

12. The composition of claim 10, wherein ethylcellulose is present during said mixing and cooling.

13. The composition of claim 7, wherein ethylcellulose is present during said mixing and said cooling.

14. A fat-coated encapsulation composition, comprising an active agent, wherein said active agent is coated with a layer, said layer comprising fat, a densifying agent, and ethylcellulose.

15. The composition of claim 14, wherein said active agent is an encapsulated active agent prepared by encapsulating said active agent by a method selected from the group consisting of spray drying, melt extrusion, coacervation, freeze drying, drum drying, belt drying, tray drying, tunnel drying, and extrusion.

16. The composition of claim 14, wherein said densifying agent is selected from the group consisting of sugars, dextrins, starches, proteins, gums, hydrocolloids, salts, celluloses, minerals, and silicas.

17. The composition of claim 14, wherein said fat is selected from the group consisting of coconut oil, palm kernel oil, lard, tallow, hydrogenated forms of liquid oils such as soybean oil, cottonseed oil, canola oil, corn oil, peanut oil, olive oil, butter oil, and chicken fat.

18. A fat-coated encapsulation composition, comprising an active agent, wherein said active agent is coated with a layer, said layer comprising fat and ethylcellulose.

19. The composition of claim 18, wherein said active agent is an encapsulated active agent prepared by encapsulating said active agent by a method selected from the group consisting of spray drying, melt extrusion, coacervation, freeze drying, drum drying, belt drying, tray drying, tunnel drying, and extrusion.

20. The composition of claim 18, wherein said fat is selected from the group consisting of coconut oil, palm kernel oil, lard, tallow, hydrogenated forms of liquid oils such as soybean oil, cottonseed oil, canola oil, corn oil, peanut oil, olive oil, butter oil, and chicken fat.

21. A method for preparing a fat-coated encapsulation composition, comprising:
   (i) mixing an active agent with a molten fat, to obtain a slurry; and
   (ii) cooling said slurry, to obtain a solid mass in which said active agent is dispersed in solid fat,
wherein ethylcellulose is present during said mixing and cooling.

22. The method of claim 21, further comprising:
   (iii) comminuting said solid mass.

23. The method of claim 22, wherein said solid mass is comminuted to a particle size of 10 $\mu$m to 2000 $\mu$m.

24. The method of claim 21, wherein said fat is selected from the group consisting of coconut oil, palm kernel oil, lard, tallow, hydrogenated forms of liquid oils such as soybean oil, cottonseed oil, canola oil, corn oil, peanut oil, olive oil, butter oil, and chicken fat.

25. The method of claim 21, wherein said active agent is an encapsulated active agent prepared by encapsulating said active agent by a method selected from the group consisting of spray drying, melt extrusion, coacervation, freeze drying, drum drying, belt drying, tray drying, tunnel drying, and extrusion.

26. The method of claim 21, wherein a densifying agent is present during said mixing and said cooling.

27. The method of claim 26, wherein said densifying agent is selected from the group consisting of sugars, dextrins, starches, proteins, gums, hydrocolloids, salts, celluloses, minerals, and silicas.

28. A fat-coated encapsulation composition, prepared by a method comprising:
   (i) mixing an active agent with a molten fat, to obtain a slurry; and
   (ii) cooling said slurry, to obtain a solid mass in which said active agent is dispersed in solid fat,
wherein ethylcellulose is present during said mixing and said cooling.

29. The composition of claim 28, further comprising:
   (iii) comminuting said solid mass.

30. The composition of claim 29, wherein said solid mass is comminuted to a particle size of 10 $\mu$m to 2000 $\mu$m.

31. The composition of claim 28, wherein said fat is selected from the group consisting of coconut oil, palm kernel oil, lard, tallow, hydrogenated forms of liquid oils such as soybean oil, cottonseed oil, canola oil, corn oil, peanut oil, olive oil, butter oil, and chicken fat.

32. The composition of claim 28, wherein said active agent is an encapsulated active agent prepared by encapsulating said active agent by a method selected from the group consisting of spray drying, melt extrusion, coacervation, freeze drying, drum drying, belt drying, tray drying, tunnel drying, and extrusion.

33. The composition of claim 28, wherein a densifying agent is present during said mixing and said cooling.

34. The composition of claim 33, wherein said densifying agent is selected from the group consisting of sugars, dextrins, starches, proteins, gums, hydrocolloids, salts, celluloses, minerals, and silicas.

35. A fat-coated encapsulation composition, prepared by a method comprising:
   (i) mixing an active agent with a molten fat, to obtain a slurry;

(ii) cooling said slurry, to obtain a solid mass in which said active agent is dispersed in solid fat; and (iii) comminuting said solid mass, wherein a densifying agent is present during said mixing and cooling.

36. The composition of claim 35, wherein said densifying agent is selected from the group consisting of sugars, dextrins, starches, proteins, gums, hydrocolloids, salts, celluloses, minerals, and silicas.

37. The composition of claim 35, wherein ethylcellulose is present during said mixing and cooling.

* * * * *